United States Patent [19]

Gordon et al.

[11] Patent Number: 5,163,438
[45] Date of Patent: Nov. 17, 1992

[54] METHOD AND APPARATUS FOR CONTINUOUSLY AND NONINVASIVELY MEASURING THE BLOOD PRESSURE OF A PATIENT

[75] Inventors: Deborah C. Gordon, Woodside; Frank A. Brunot, Livermore, both of Calif.

[73] Assignee: Paramed Technology Incorporated, Mountain View, Calif.

[21] Appl. No.: 586,794

[22] Filed: Sep. 24, 1990

Related U.S. Application Data

[63] Continuation of Ser. No. 270,224, Nov. 14, 1988, Pat. No. 4,960,128.

[51] Int. Cl.⁵ ............................................... A61B 8/00
[52] U.S. Cl. .................................... 128/677; 73/1 DV
[58] Field of Search ................................. 128/680-683, 128/660.02, 24 A; 73/1 DV

[56] References Cited

U.S. PATENT DOCUMENTS

| | | | |
|---|---|---|---|
| 3,885,551 | 5/1975 | Massie | 128/660.02 X |
| 4,250,894 | 2/1981 | Frei et al. | 128/774 |
| 4,791,915 | 12/1988 | Barsotti et al. | 128/24 AA |

*Primary Examiner*—Francis Jaworski
*Attorney, Agent, or Firm*—Limbach & Limbach

[57] ABSTRACT

In the present invention, a method and an apparatus for measuring the blood pressure of a patient continuously and non-invasively is disclosed. The blood pressure is determined by measuring the harmonic frequencies and displacements of an arterial wall of the patient. The measurements are then calibrated against an absolute blood pressure supplied by an operator at a particular time. The blood pressure is then the sum of the relative changes of the measurements and the absolute blood pressure.

2 Claims, 5 Drawing Sheets

FIG. 2a  SENSOR SIGNAL CONDITIONING AND DIGITIZING

FIG. 2b  DIGITAL SIGNAL MICROPROCESSOR

METHOD AND APPARATUS FOR CONTINUOUSLY AND NONINVASIVELY MEASURING THE BLOOD PRESSURE OF A PATIENT

This is a continuation of application Ser. No. 07/270,224, filed Nov. 14, 1988 and now U.S. Pat. No. 4,960,128.

TECHNICAL FILED

The present invention relates to a method and an apparatus for continuously and non-invasively measuring the blood pressure of a patient and, more particularly, the present invention relates to measuring the harmonic frequencies and displacement components of an arterial wall, and converting the measurements into a waveform signal emulating the signal from an invasive arterial sensor.

BACKGROUND OF THE INVENTION

Methods and apparatuses for the detection of the blood pressure of a patient are well-known in the art. One type of apparatus involves the use of an invasive arterial line. In an arterial line device, a sensor is inserted into the artery of a patient. The signal from the arterial sensor is supplied to a patient monitor which calculates, among other parameters, the blood pressure of a patient. The patient monitor is also capable of sending a signal to the sensor to determine if the sensor is electrically connected to the patient monitor. Although such apparatuses provide continuous and accurate blood pressure data, there are many disadvantages. First, there is a potential risk of infection. Further, the procedure is costly and consumes valuable health care takers' time, in that it is a surgical procedure involving the insertion of a catheter into a patient's artery. In addition, the patient experiences discomfort.

In the area of non-invasive devices, one prior art teaches the automatic expansion of pressure cuffs and the measurement of the blood pressure based thereon. However, such devices can only be used intermittently. Prolonged and frequent use can lead to patient discomfort.

U.S. Pat. No. 4,669,485 teaches using two cuffs to measure the blood pressure of a patient. The absolute blood pressure of the patient is initially measured. Thereafter, the second cuff is maintained at a low pressure, continuously, to monitor continuously the relative blood pressure of the patient. In this manner, the blood pressure of the patient can be continuously monitored. However, such a device still involves using blood pressure cuffs, which can be a source of discomfort to the patient and the device is subject to patient motion and as a consequence degraded results.

In column 4, lines 39-column 5, line 3 of U.S. Pat. No. 4,669,485, reference is made to yet another prior art non-invasive device which measured the arterial wall displacement and used those measurements to determine the relative blood pressure. However, the use of only the displacement measurement is subject to error.

Reference is also made to U.S. Pat. No. 3,318,303. In that reference, the output of an external microphone sensor is used to determine the blood pressure of a patient. In particular, the so-called "Korotkoff" sound may be determined.

U.S. Pat. No. 4,203,451 discloses that a data processor can be used to receive signals from the Carotid transducer.

U.S Pat. No. 3,773,033 discloses the use of an arterial vibration sensor to monitor the performance of the heart and arteries during a succession of cardiac cycles. However, a pressure cuff also applies variable pressure to a specified artery being monitored by the arterial vibration sensor.

Heretofore, none of the prior art devices or references has suggested a non-invasive apparatus for continuously and accurately measuring the blood pressure of a patient using data obtained from the arterial wall, thereby providing for greater patient comfort. Further, none of the prior art devices has checked for the integrity of the sensor, apart from it being merely electrically connected to the monitor.

SUMMARY OF THE INVENTION

In the present invention, an instrument for continuously and non-invasively measuring the blood pressure of a patient is disclosed. The instrument has a non-invasive sensor for measuring continuously the frequencies and displacements of an arterial wall and for generating continuously a first signal in response thereto. The first signal is processed continuously to produce a continuous processed first signal. The instrument further receives a calibration signal which is indicative of the absolute blood pressure of the patient at a particular point in time. The processed first signal corresponding to the particular point in time is stored. Finally, the instrument compares continuously the continuous processed first signal to the stored processed first signal and generates continuously a signal indicative of the continuous blood pressure of the patient.

DETAILED DESCRIPTION OF THE DRAWINGS

Figure 1:
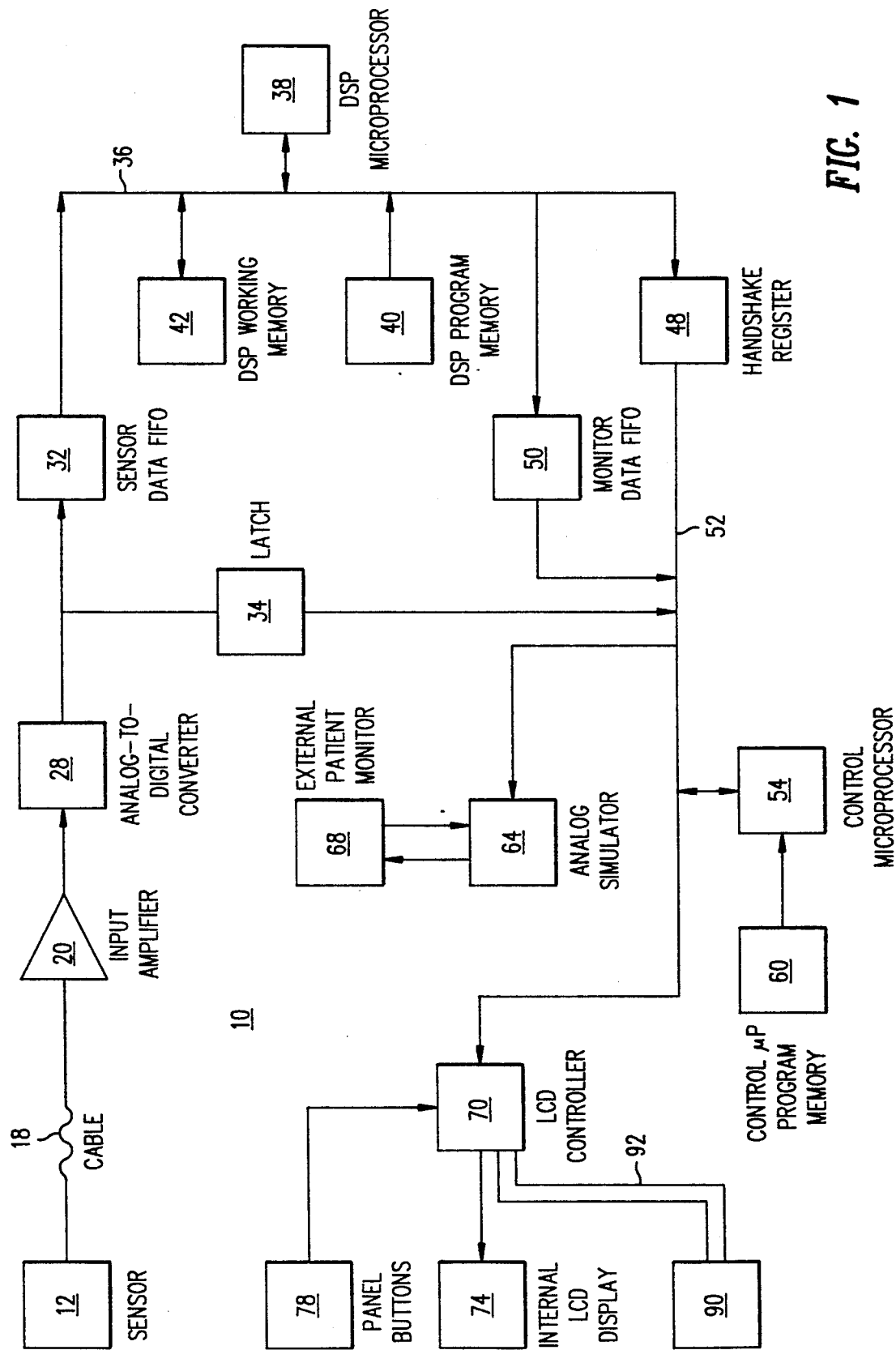
FIG. 1 is a block level diagram of the apparatus of the present invention.
Figure 2:
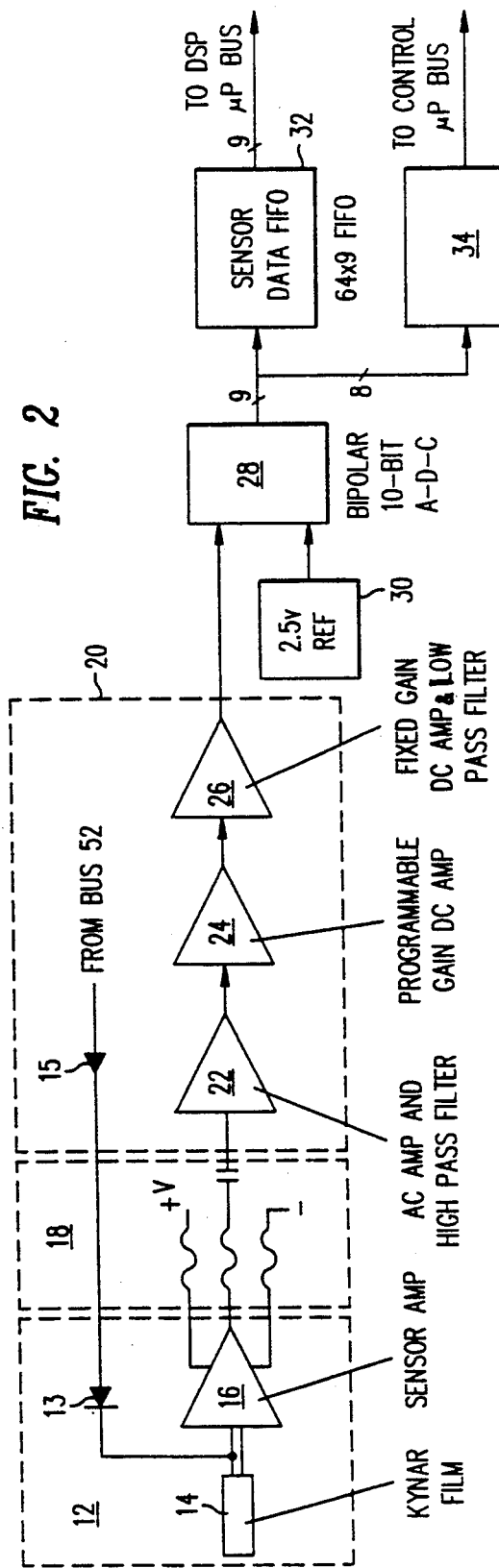
FIG. 2(a-d) are detailed schematic diagrams of various portions of the apparatus shown in FIG. 1.
Figure 2:
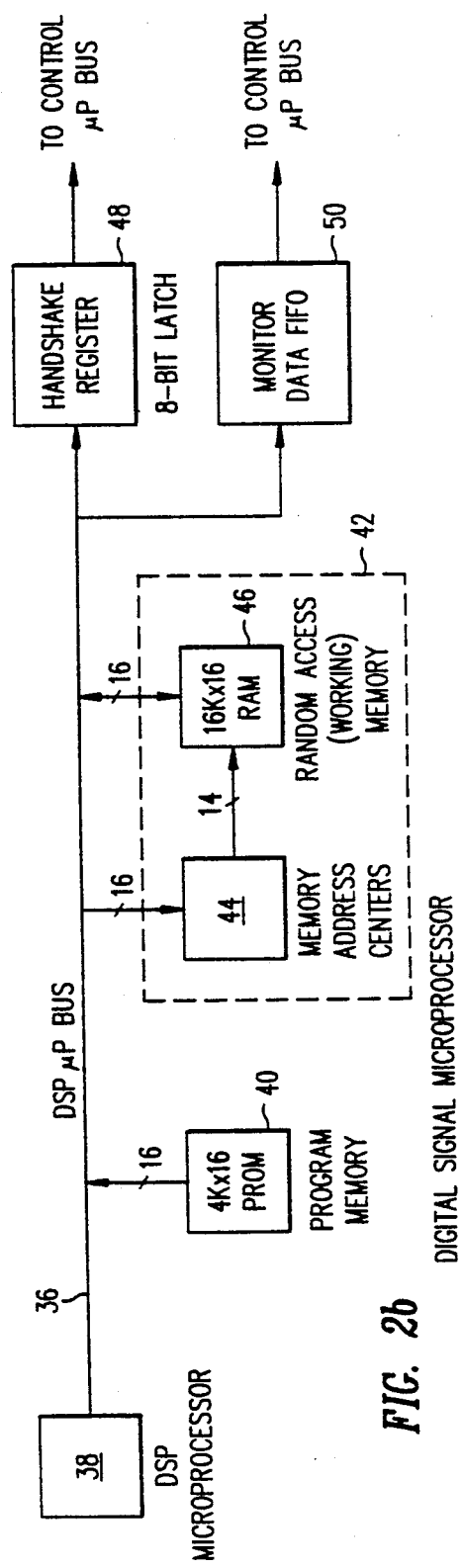
Figure 2C:
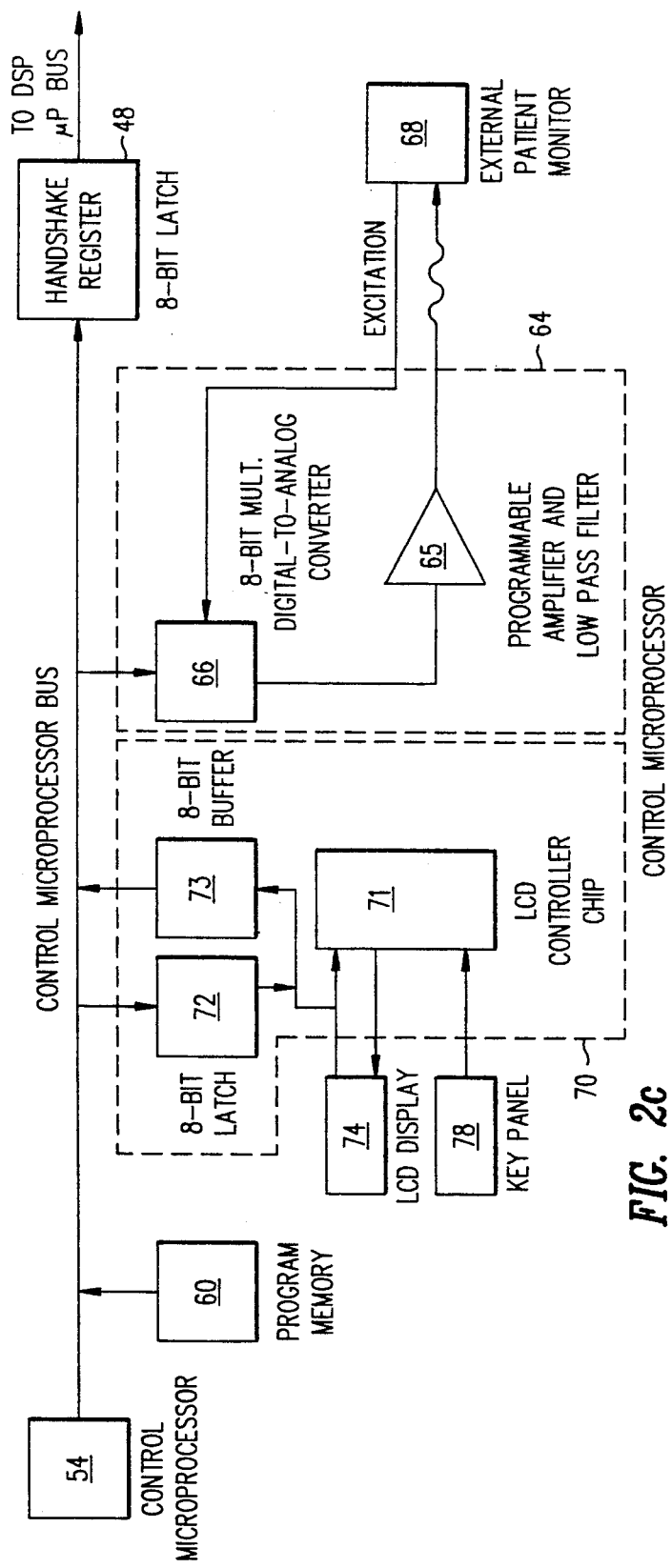
Figure 2D:
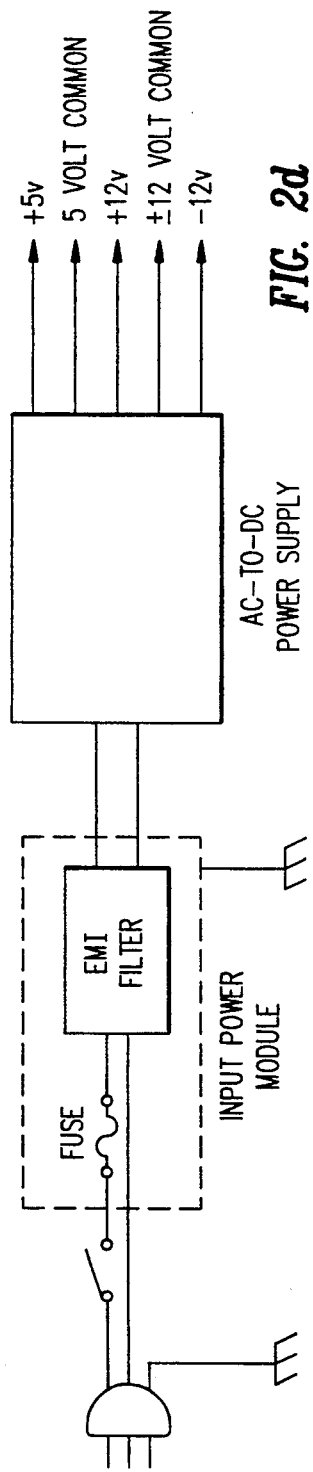

Referring to FIG. 1, there is shown a block diagram of an apparatus 10 of the present invention. The apparatus 10 comprises a sensor assembly 12 which measures continuously, with time, the external displacement and the harmonic frequencies of the displacement caused by the lateral expansion of an arterial wall of a patient. The pattern of expansions and contractions is reflective of the changes in the pressure wave at this site in the arterial system. In one embodiment, the sensor assembly 12 has a piezoelectric sensing material, such as Kynar film 14. The Kynar film 14 generates a signal which is directly coupled to a sensing amplifier 16, located within the sensor assembly 12. The sensing amplifier 16 transforms the impedance of the signal from a high value, on the order of several megohms of the sensing film 14, to a low value which can be transmitted over a cable 18 (typically on the order of 10 feet). The sensor assembly 12 is positioned at any site of a patient where the artery is close to the surface of the skin, such as over the radial artery.

The sensing film 14 can be excited by an excitation signal supplied from the control microprocessor 54 through the control microprocessor bus 52, through an amplifier 15 and through the cable 18 to a diode 13. The excitation signal causes the film 14 to mechanically transduce, i.e. flex. The excitation signal is applied momentarily (on the order of one microsecond), and is thereafter removed. Because the sensing film 14 will have been flexed by the excitation signal, upon removal of the excitation signal, the sensing film 14 will resonate and move in the opposite direction. This movement in the opposite direction causes the production of a response electrical signal which is supplied along the cable 18. The detection of this response signal indicates that the sensing film 14 is not only electrically connected and is adapted to transduce, but is also in fact electromechanically ready to transduce the arterial wall movements.

Figure 3A:
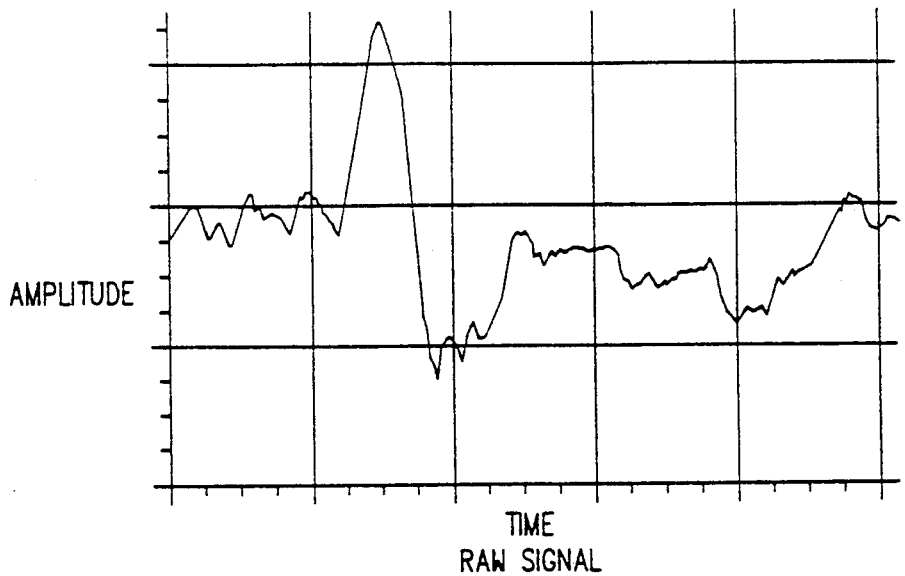
FIG. 3(a-f) are schematic diagrams showing representative waveform signals processed and generated by the apparatus of the present invention.

The sensor assembly 12 is then positioned to detect arterial wall motion. The signal detected by the sensor assembly 12, caused by the motion of the arterial wall, is then supplied to an input amplifier 20 which removes any DC component from the signal (FIG. 3a). The input amplifier 20 comprises an AC voltage amplifier and high pass filter 22 which receives the signal from the cable 18 and supplies an output thereof to a programmable gain DC voltage amplifier 24. The purpose of the programmable gain DC voltage amplifier 24 is to compensate for variations in the sensitivity of different sensors and physical variations among different patients. The output of the programmable gain DC voltage amplifier 24 is then supplied to a fixed gain DC amplifier and low pass filter 26. The DC amplifier and low pass filter 26 provides an output which is supplied to an analog-to-digital converter 28. The output of the input amplifier 20 is set to optimize the signal of the analog-to-digital converter 28.

The analog-to-digital converter 28 is a bipolar 10-bit A-to-D converter which receives a reference voltage 30 of 2.5 volts. The analog-to-digital converter 28 digitizes the input analog signal at the rate of approximately 250 hertz or one conversion each four milliseconds.

The output of the bipolar analog-to-digital converter 28 is then supplied to a first-in-first-out (FIFO) buffer 32. The data is stored in the FIFO buffer 32 until a predetermined number of samples are collected. In one embodiment, the apparatus 10 of the present invention waits until there are 16 samples in the FIFO buffer 32 before the data from the FIFO buffer 32 are read out and are supplied to the DSP microprocessor bus 36 and are then further processed.

Further, the eight most significant bits (MSB) of the ten bits from the analog-to-digital converter 28 of each sensor sample are stored in an 8-bit latch 34. The output of the 8-bit latch 34 is supplied to the control microprocessor bus 52 and can be supplied to an external or internal display screen 74. By outputting the relative signal strength of the sensor assembly 12 and displaying it on the display 74, the apparatus 10 permits the operator to move the sensor assembly 12 to optimally place the sensor assembly 12 on the patient.

After the FIFO buffer 32 is filled with the predetermined number of digitized sensor samples, the digital signal processor (DSP) 38 is interrupted. The contents of the FIFO buffer 32 is then transferred to the DSP microprocessor bus 36 and into the DSP working memory 42. In one embodiment, the DSP working memory 42 comprises 16K by 16 bits of random access memory (RAM) 46 and two multiplexed memory address counters 44. One memory address counter addresses RAM 46 when writing data to the RAM 46. The other memory address counter addresses RAM 46 when reading data from RAM 46. Each counter can be set to automatically increment or decrement after a read or write operation is completed. This increases processing throughput, since the DSP microprocessor 38 does not have to address each operation. The memory address counters 44 supply 14 address lines to address the 16K by 16 RAM memory 46. The DSP microprocessor 38 is under the control of a program which is stored in a program memory 40. The DSP microprocessor 38 is a TMS-32010 made by Texas Instruments. The program memory 40 comprises 4K by 16 bits of PROM.

The program stored in the program memory 40 controls the DSP processor 38 to process the data from the FIFO buffer 32 to convert the sensor data into data values of a signal representative of the output blood pressure. A copy of the program is attached herewith as Exhibit A. The function of the program stored in the program memory 40 will be described hereinafter.

After the DSP microprocessor 38 has completed the processing of the sensor signal data from the FIFO buffer 32 and into a waveform signal data, the waveform signal data are passed to and stored in the monitor data FIFO buffer 50.

From the monitor data FIFO buffer 50, the computed points of the waveform signal may be directed to display on the display screen 74. The handshake register 48 links the DSP microprocessor 38 with the control microprocessor 54, by means of the DSP bus 36 and the control bus 52. Both data and control commands can be passed between the two processors by this register 48. Since the monitor data FIFO buffer 50 is loaded with and relieved of data at the same rate as the original sensor data FIFO buffer 32, the computed points which comprise the waveform are displayed at the rate of one data point for each four milliseconds.

The control microprocessor 54 also operates under a program which is stored in the program memory 60. A copy of that program is attached herewith as Exhibit B. The control microprocessor 54 is a 80C31 made by Intel Corporation.

The apparatus 10 of the present invention can also supply the waveform signal data from the DSP microprocessor 38 to an external patient monitor 68. When the apparatus 10 functions in this manner, it is acting as an arterial sensor emulator, i.e. to the patient monitor 68, the signal supplied thereto is no different than the signal generated by an arterial sensor. The data is supplied to an eight-bit multiplying digital-to-analog converter 64 which emulates a normal dome pressure transducer, which is conventionally used to convert invasive arterial line fluid pressure sensor to electrical signals for input to the patient monitor 68. The monitor 68 outputs its normal excitation voltage and, in turn, receives an input signal of the expected sensitivity expressed as microvolts output per volt of excitation per millimeter of mercury of pressure from the analog simulator 64.

The analog simulator 64 consists of an 8-bit multiplying digital-to-analog converter 66, which converts digital values received from the monitor data FIFO buffer 50 sent along the control bus 52, into an analog signal, required by the external patient monitor 68. The programmable amplifier/low pass filter 65 varies the output level of the analog signal in accordance with the input sensitivity of the particular patient monitor 68 being used. Thus, some of the commonly used patient monitors 68 require the following input sensitivities:

Hewlett-Packard: 5 uv input/volt of excitation/mm Hg.

Marquette: 20 uv input/volt of excitation/mm Hg.

In the operation of the apparatus 10 of the present invention, the apparatus 10 is initially placed in a calibration mode. In this calibration mode, the operator identifies the patient monitor 68 with which the apparatus 10 is connected through the analog simulator 64. The selection of the particular patient monitor 68 sets the programmable amplifier 65 to the correct output voltages.

Thereafter, the apparatus 10 sends to the patient monitor 68 a signal that the patient monitor 68 expects during the venting of the arterial line dome that is normally connected to the arterial line port. When the operator confirms the completion of the above steps, the apparatus 10 then shifts into the next mode of operation, the acquire mode.

In the acquire mode, the apparatus 10 provides a check that the sensor assembly 12 is connected to the apparatus 10. As previously discussed, this includes supplying the excitation signal and the detection of the response signal. The detection of the response signal from the sensing film 14 indicates that the sensor assembly 12 is electrically connected and the sensing film 14 is electromechanically operational. The apparatus 10 acquires and displays the raw pulse vibration signal that the sensor assembly 12 detects for the purpose of positioning the sensor assembly 12 optimally. Upon command by the operator, the apparatus 10 acquires and stores the previous four-second segment of the pulse vibration signal for correlation with the starting blood pressure values.

Figure 3B:
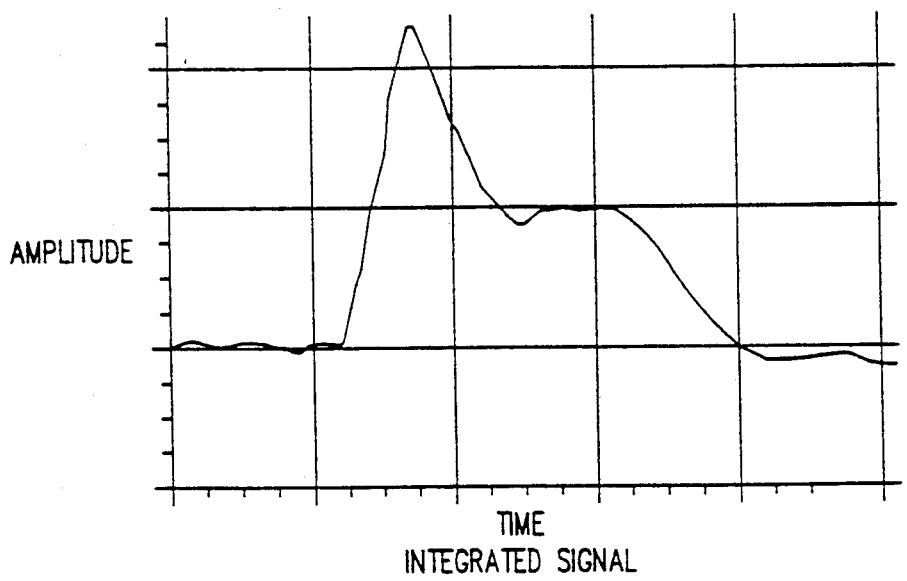
Figure 3C:
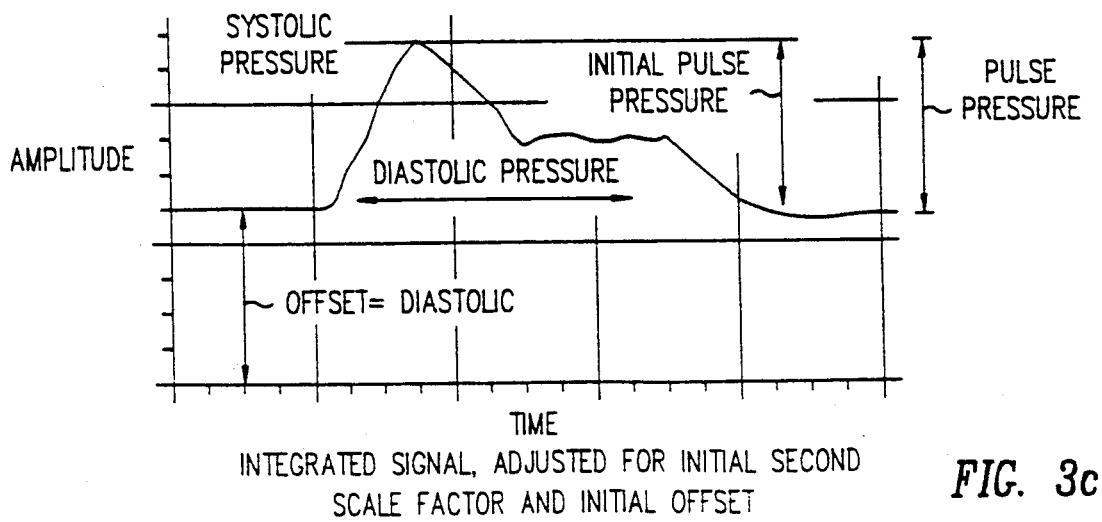
Figure 3D:
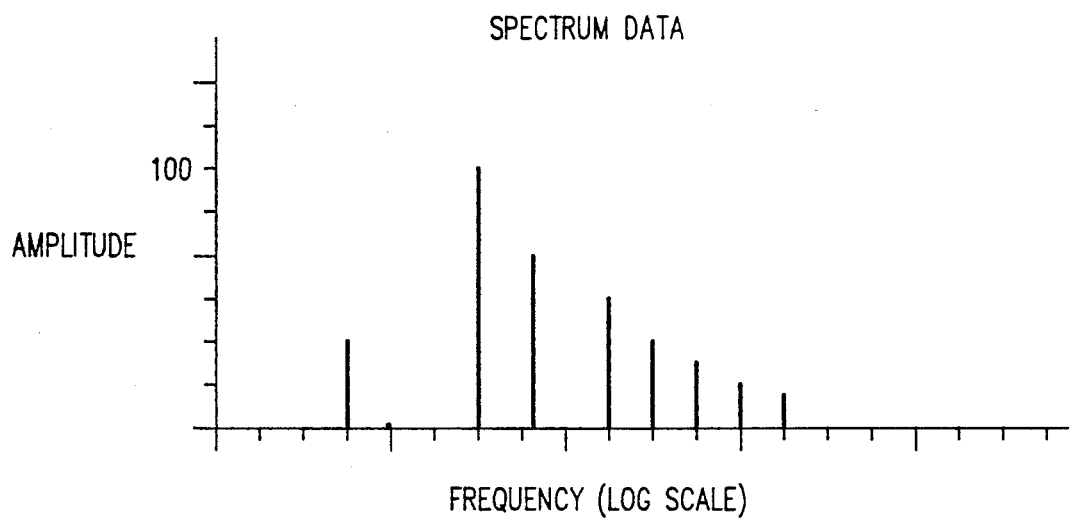

The DSP microprocessor 38 then processes the signal corresponding to the four-second segment from the FIFO buffer 32. The DSP microprocessor 38 determines the characteristic components of the input signal in accordance with the following steps:

1. The input signal comprising approximately four (4) seconds of data at a sample frequency of 4 milliseconds is stored in the working memory 42 (FIG. 3a).
2. The input signal is fast fourier transformed at approximately 0.25 Hz. interval from approximately 0-250 Hz., thereby generating 1024 frequency values, with each frequency value having an amplitude value (FIG. 3d).
3. The frequency that corresponds to the maximum amplitude value is determined.
4. All the amplitudes of the spectrum data are normalized to the frequency found in step 3, with that amplitude as 100.
5. The normalized fast fourier transformed signal is stored in the working memory 42.

After the DSP microprocessor 38 has completed the processing of the sensor signal from the FIFO buffer 32 the apparatus 10 shifts to the BP input mode.

In the BP input mode, the apparatus 10 requests the operator to input the patient's absolute blood pressure values as measured by an independent blood pressure apparatus. The absolute blood pressure values may be manually determined by a health care worker and entered into the apparatus 10 via the panel buttons 78. Alternatively, the absolute blood pressure values may be supplied from a conventional, well known, automatic blood pressure monitor 90, such as a pressure cuff measuring instrument 90. The data from the blood pressure monitor 90 is supplied to the apparatus 10 along an RS-232 input line 92, to the LCD controller 70, just like the inputs from the panel buttons 78. Since the apparatus 10 of the present invention 10 requires correlation with absolute blood pressure value only during the initial stage, the automatic blood pressure monitor 90, even if it were of pressure cuff design, would not pose the disadvantages of continual use.

The absolute blood pressure values correspond to the correlated, stored four-second segment sensed by the sensor assembly 12. When the operator confirms the conclusion of the input blood pressure value, the DSP microprocessor 38 performs the following steps:

a. The four-seconds of data stored in memory 42 (from step 1, above) are integrated (FIG. 3b).
b. A first scale factor is calculated. The first scale factor is chosen such that the maximum absolute amplitude of the waveform signal found in step a times the first scale factor would equal the pulse pressure (pulse pressure=systolic—diastolic) (FIG. 3c).
c. An offset (equal to the diastolic) is added to the waveform of step b (FIG. 3c).
d. The processed waveform signal from step c is stored in the memory 42.

In sum, during the input mode, the DSP microprocessor 38 calculates the first scale factor and the offset. The waveform generated by the apparatus 10 (from step c), after passing through the analog simulator 64, would be as if the waveform signal were generated by an invasive arterial sensor. Thus, the apparatus 10 emulates an invasive arterial sensor. The apparatus 10 then enters into the monitor mode.

In the monitoring mode, the apparatus 10 continuously receives the signal from the output of the sensor assembly 12 and continuously processes that signal via the input amplifier 20, digital-to-analog converter 28 and the sensor data FIFO buffer 32. The DSP microprocessor 38 continuously processes the digitized signal in the following manner.

Figure 3E:
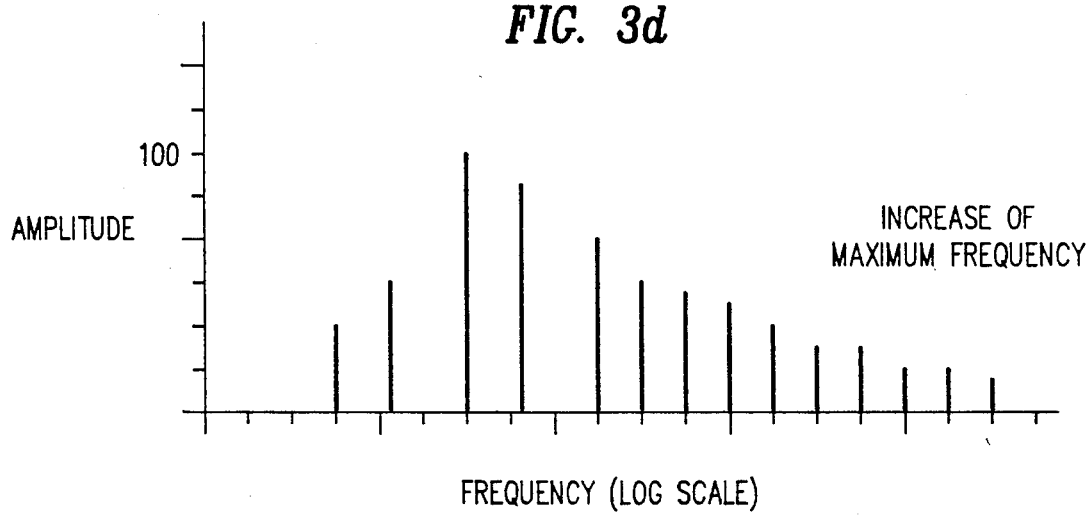
Figure 3F:
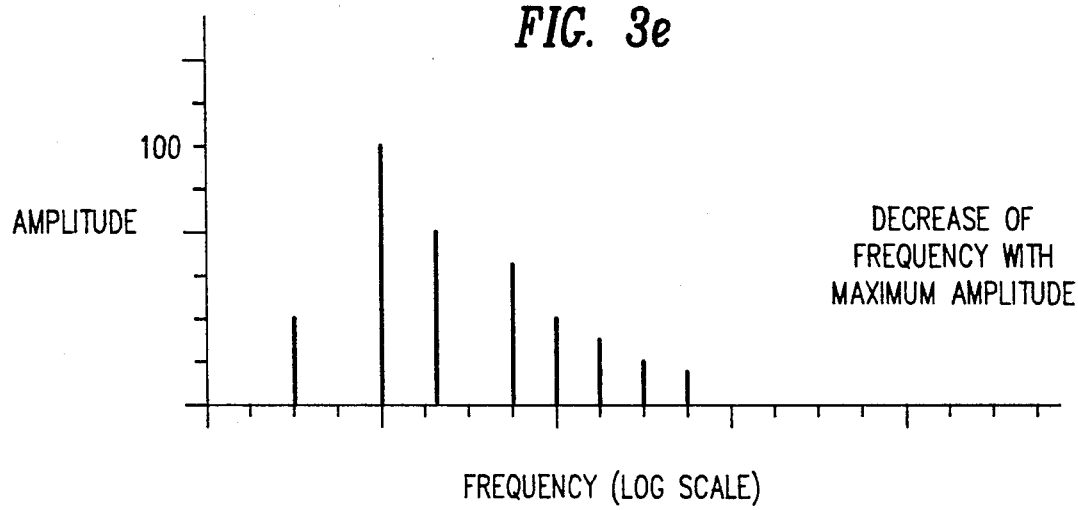

6. The digitized signal from the FIFO buffer 32 is processed in accordance with steps 1–5 above.
7. The normalized frequency spectrum of the current signal from step 6 is subtracted from the normalized frequency spectrum of the initial signal, as stored in working memory 42 (FIG. 3e or 3f).
8. A comparison is made between the maximum frequency of the normalized frequency of the current signal and of the initial signal.
9. The change in the amount of the maximum frequency is noted and is supplied to the following look up table, and the corresponding second scale factor is determined:

| Change of Maximum Frequency | Second Scale Factor |
| --- | --- |
| 50% | 85% |
| 67% | 90% |
| 83% | 95% |
| 100% | 100% |
| 133% | 105% |
| 167% | 110% |
| 200% | 115% |

10. A comparison is made between the frequency of the maximum amplitude of the current signal to the initial signal. For each shift in frequency (+ or −) of 1 Hz., the offset (determined from step c) is adjusted correspondingly to yield a change of 5 mm Hg. Thus, if the frequency of the maximum amplitude of the current signal is increased 1 Hz. from the frequency of the maximum amplitude of the initial signal, the offset for the initial signal is increased by an amount equal to 5 mm Hg.

11. The data points from the FIFO buffer 32 are integrated.

12. The data points from step 11 are multiplied by the first scale factor and by the second scale factor, and the new offset (from step 10) is added to the resultant waveform signal.

The points that represent the waveform signal (step 12) are supplied to the monitor data FIFO buffer 50 and then to the analog simulator 64 or LCD controller 70 for display on the external patient monitor 68 or internal LCD display 74. The steps of 6–12 are repeated for each new four-second segment of data.

In another embodiment of the present invention, the health care worker can supply operating limits to the apparatus 10 by way of the input panel buttons 78. When the current signal, processed by the DSP microprocessor 38, is outside of the operating limits, an alarm can be sounded to alert the health care worker. Alternatively, the LCD controller 70 can initiate a control signal to the automatic blood pressure monitor 90 to re-initiate the apparatus 10.

From the foregoing, it can be seen that a highly accurate and efficient blood pressure measuring apparatus and method has been disclosed.

What is claimed is:

1. A medical instrument comprising:
   an electromechanical sensing means for generating a signal in response to mechanical motion detected by said sensing means, and for moving in response to an electrical signal supplied thereto;
   means for supplying an excitation signal to said sensing means to cause motion in said sensing means; and
   means for detecting a response signal generated by said sensing means moving in response to said excitation signal supplied thereto,
   wherein said detection of said response signal is indicative of the operational readiness of said sensing means.

2. A method of testing the operational readiness of an electromechanical sensing means for placement on a particular location of a patient, said sensing means generating a response signal in response to the detection of mechanical motion of said sensing means, said sensing means also moving in response to an excitation signal applied thereto; said method comprising the steps of:
   positioning said sensing means on said patient;
   supplying an excitation signal to said sensing means;
   moving said sensing means in response to said excitation signal; and
   detecting said response signal in response to the movement of said sensing means,
   wherein the detection of said response signal is indicative of the operational readiness of the sensing means.

* * * * *